United States Patent
Kealey et al.

Patent Number: 5,378,455
Date of Patent: Jan. 3, 1995

[54] COSMETIC COMPOSITION FOR INHIBITING HAIR GROWTH

[75] Inventors: George T. E. Kealey, Cambridge; Gillian E. Westgate, Irthlingborough; Rebecca Williams, Cambridge, all of England

[73] Assignee: Chesebrough-Ponds USA Co., Division of Conopco, Inc., Greenwich, Conn.

[21] Appl. No.: 173,261

[22] Filed: Dec. 27, 1993

Related U.S. Application Data

[63] Continuation of Ser. No. 937,795, Aug. 28, 1992, abandoned.

[30] Foreign Application Priority Data

Sep. 4, 1991 [GB] United Kingdom ............... 918866

[51] Int. Cl.⁶ ........................................... A61K 7/06
[52] U.S. Cl. ........................... 424/73; 424/62; 424/70.1; 424/401; 424/70.6
[58] Field of Search ....................... 424/70, 73

[56] References Cited

U.S. PATENT DOCUMENTS

| | | | |
|---|---|---|---|
| 4,720,489 | 1/1988 | Shander | 514/171 |
| 5,095,007 | 3/1992 | Ahluwalia | 514/23 |
| 5,158,976 | 10/1992 | Rosenberg | 514/561 |

FOREIGN PATENT DOCUMENTS

WO88/08295 11/1988 WIPO .

OTHER PUBLICATIONS

Philpott, et al. "Human Hair Growth in vitro" Journal of Cell Science 97, (1990) pp. 463–471.

*Primary Examiner*—Thurman K. Page
*Assistant Examiner*—James M. Spear
*Attorney, Agent, or Firm*—Rimma Mitelman

[57] ABSTRACT

A composition suitable for topical application to mammalian skin for reducing, retarding or eliminating hair growth is provided, which comprises:

i) an effective amount of an inhibitor of glutamine metabolism in mammalian skin or hair; and ii) a cosmetically acceptable vehicle for the inhibitor.

16 Claims, 1 Drawing Sheet

Fig.1.

COSMETIC COMPOSITION FOR INHIBITING HAIR GROWTH

This is a continuation application of Ser. No. 07/937,795, filed Aug. 28, 1992, now abandoned.

FIELD OF THE INVENTION

The invention relates to a composition for topical application to mammalian skin or hair for reducing or retarding hair growth, or for eliminating unwanted hair from the mammalian body surface.

BACKGROUND TO THE INVENTION

In recent years, there has been great emphasis on the promotion, enhancement, or at least maintenance of normal hair growth on the human head, particularly with men whose hair has started to recede, as in male pattern baldness, or with both men and women, as hair becomes thinner with advancing age. To this end, the market in "hair restorers" or "baldness cures" is growing.

There has also for many years existed a demand for products which are capable of removing unwanted hair, particularly from other parts of the body, such as the legs, armpits and face, without recourse to shaving. This demand has been greater for women than for men, although men would undoubtedly welcome a means for permanently or semi-permanently removing hair from the face, if only to avoid the daily need to shave.

The products that are currently available for topical use in the removal of unwanted hair are mostly based on thioglycollates as the active ingredient. Examples are those available under the trade names VEET and NAIR. Thioglycollates function in this role as reducing agents at high pH, by reducing disulphide bonds in hair, following penetration into the follicular canal, where the hair is weakened in the region above the keratinizing zone. The hair shaft can then break off just below the skin surface leaving a soft., smooth surface feel to the skin.

Hair growth does not however cease and, since the hair is broken near the skin surface, regrowth occurs within a relatively short time and the cosmetic advantage is thus rapidly lost. Retreatment with the thioglycollate product is then necessary, if the treated skin is to be maintained in a hairless condition.

There is consumer resistance to the use of thioglycollate hair removal product as skin irritation is sometimes encountered, but as no alternative methods of hair removal exist, apart from shaving and plucking of individual hairs, vanity demands that thioglycollate-containing products offer the most effective method, particularly for women, for the removal of unwanted hair from the body surface.

It is well established that in most mammals, including man, hair does; not grow continuously, but undergoes a cycle of activity involving alternate periods of growth and rest. The hair growth cycle can be divided into three main stages, namely:
i) an active stage known as anagen, during which the hair follicle penetrates deep into the dermis with the cells of the bulb dividing rapidly and differentiating to form the hair,
ii) a regressive stage known as catagen, which is heralded by the cessation of mitosis, and during which the follicle regresses upwards through the dermis and hair growth ceases, and
iii) a resting stage known as telogen, in which the regressed follicle contains a small secondary germ with an underlying ball of tightly packed dermal papilla cells.

The metabolism of the hair follicle during growth is not well understood. It has been established on microdissected hair follicles that glucose is a major fuel which the hair follicle requires for normal growth and that glucose is not oxidized to any great extent, as most of it is converted to lactate. [See, for example, Adachi K, Uno H. Glucose Metabolism of Growing and Resting Hair Follicles. Am J Physiol (1968) 215, 1234–1239; and Philpott M P, Kealey T, Metabolic Studies on Isolated Hair Follicles. J Invest Derm (1991) 96, 875–879].

In more recent work, we have shown that surprisingly, the hair follicle metabolises very little lipid fuels. Instead, glutamine has emerged as a major fuel which yields as much energy to the hair follicle as does glucose. We have also shown that glutamine is largely metabolized to lactate, and that the rate of hair growth in vitro will only match that seen in vivo if both glucose and glutamine fuels are present at the same time.

Armed with this new knowledge that glutamine is important to normal hair growth, we have now shown that in in vitro experiments, the use of certain inhibitors which prevent glutamine from being converted to lactate also interfere with hair growth. It follows, that by careful selection of an inhibitor of at least one of the steps in the glutamine-lactate metabolic pathway, particularly that concerned with converting glutamine to pyruvate, topical application of the inhibitor can reduce or retard hair growth, or even eliminate hair growth altogether.

The invention is accordingly concerned with the selection of one or more substances that will modulate mammalian hair growth by inhibiting at least one of the enzymes involved in glutamine metabolism.

It is furthermore envisaged that these substances can be employed in one of several treatments for eliminating unwanted hair from the body surface, or at least in reducing its rate of growth, such as:
i) a two step treatment in which hair is first removed by a conventional method and then regrowth prevented, or retarded by subsequent application of the substance; or
ii) a one step treatment in which the rate of hair growth is reduced, by application of the substance, without necessarily being accompanied by consequential hair loss, for example in beard growth.

The invention is accordingly also concerned with the use of inhibitors of glutamine metabolism in the hair follicle, in retarding or eliminating hair growth.

DEFINITION OF THE INVENTION

Accordingly, the invention provides a composition which is suitable for topical application to mammalian skin or hair for reducing or retarding hair growth or for eliminating hair from the skin, which composition comprises:
i) an effective amount of an inhibitor of glutamine metabolism in the hair follicle; and
ii) a cosmetically acceptable vehicle for the inhibitor.

DISCLOSURE OF THE INVENTION

The invention is concerned with the selection of an inhibitor of glutamine metabolism in mammalian skin or hair, and its topical application for the purpose of reducing or retarding hair growth or for eliminating hair growth altogether from those parts of the mammalian body where unwanted hair exists.

The Inhibitor of Glutamine Metabolism

The pathway by which glutamine is converted to pyruvate is shown in the diagram below, the pathway comprising a series of intermediates, each of which results from the activity of a selective enzyme, as will be explained later in this specification.

The composition according to the invention comprises an inhibitor of at least one enzyme involved in the conversion of glutamine to pyruvate.

Each step in the conversion of glutamine to pyruvate as shown in the above diagram is controlled by a specific enzyme, and therefore by introduction of an inhibitor for at least one of these specific enzymes, glutamine to pyruvate conversion can be halted or at least retarded and, as a consequence, hair growth reduced, retarded or even eliminated. This can be achieved by topical application to relevant areas of skin and hair of a composition comprising one or more selected inhibitors.

The inhibitor of glutamine metabolism can accordingly be selected from one or more of the following, dependent upon the enzyme to be inhibited.

As can be seen from the diagram, glutamine is first converted to glutamate, and the relevant enzyme here is glutaminase. An example of a suitable glutaminase inhibitor is 6-diazo-5-oxonorleucine.

Glutamate is then converted to α-ketoglutarate, and the relevant enzyme here is glutamate dehydrogenase. An example of an inhibitor of glutamate dehydrogenase is 3-carboxy-5-bromofuroic acid.

α-ketoglutarate is then converted to succinyl CoA, and the relevant enzyme here is α-ketoglutarate decarboxylase. An example of a α-ketoglutarate decarboxylase inhibitor is a source of copper ions, such as copper (II) acetate.

Succinyl CoA is then converted to succinate, and the relevant enzyme here is succinyl CoA synthetase. An example of a succinyl CoA synthetase inhibitor is vanadium sulphate.

Succinate is then converted to fumarate and the relevant enzyme here is succinate dehydrogenase. An example of a succinate dehydrogenase inhibitor is malonic acid.

Fumarate is then converted to malate, and the relevant enzyme here is fumarase. An example of a suitable fumarase inhibitor is meso-tartaric acid.

Malate is then converted to oxaloacetate and the relevant enzyme here is malate dehydrogenase. An example of a suitable malate dehydrogenase inhibitor is fluoromalic acid.

Oxaloacetate is then converted to pyruvate and the relevant enzyme here is malic enzyme. An example of a suitable malate enzyme inhibitor is hydroxymalonic acid, also referred to as tartronic acid.

Malate can also be converted directly to pyruvate, and the relevant enzyme here is malic enzyme. An example of a suitable malate enzyme inhibitor is hydroxymalonic acid.

The enzyme inhibitors mentioned are examples of suitable inhibitors of the relevant enzymes which play a part in the conversion of glutamine to pyruvate. It is understood that other enzyme inhibitors can be employed in the composition of the invention.

The amount of the selected enzyme inhibitor that can be employed in the composition according to the invention for topical application to skin or hair in order to prevent or at least retard conversion of glutamine to pyruvate is an effective amount which can be determined by the man skilled in the art.

It has been found out that surprisingly small amounts are sufficient for the inhibitor to be affective. Evidence for this unexpected efficacy is given later herein.

Accordingly the composition comprises preferably not more than 5.0 weight parts inhibitor, and more preferably not more than 1.0 weight parts inhibitor per 100 volume parts of the composition.

The Cosmetically Acceptable Vehicle

The composition according to the invention also comprises a cosmetically acceptable vehicle to act as a diluent, dispersant or carrier for other materials present in the composition, so as to facilitate their distribution when the composition is applied to the mammalian skin and/or hair.

Vehicles other than water can include liquid or solid emollients, solvents, humectants, thickeners and powders. Examples of each of these types of vehicle, which can be used singly or as mixtures of one or more vehicles, are as follows:

Emollients, such as stearyl alcohol, glyceryl monoricinoleate, mink oil, cetyl alcohol, isopropyl isostearate, stearic acid, isobutyl palmitate, isocetyl stearate, oleyl alcohol, isopropyl laurate, hexyl laurate, decyl oleate, octadecan-2-ol, isocetyl alcohol, eicosanyl alcohol, behenyl alcohol, cetyl palmitate, silicone oils such as dimethylpolysiloxane, di-n-butyl sebacate, isopropyl myristate, isopropyl palmitate, isopropyl stearate, butyl stearate, polyethylene glycol, triethylene glycol, lanolin, cocoa butter, corn oil, cotton seed oil, olive oil, palm kernel oil, rapeseed oil, safflower seed oil, evening primrose oil, soybean oil, sunflower seed oil, avocado oil, sesame seed oil, coconut oil, arachis oil, castor oil, acetylated lanolin alcohols, petroleum jelly, mineral oil, butyl myristate, isostearic acid, palmitic acid, isopropyl linoleate, lauryl lactate, myristyl lactate, decyl oleate, myristyl myristate;

Propellants, such as propane, butane, isobutane, dimethyl ether, carbon dioxide, nitrous oxide;

Solvents, such as ethyl alcohol, methylene chloride, isopropanol, acetone, ethylene glycol monoethyl ether, diethylene glycol monobutyl ether, diethylene glycol monoethyl ether, dimethyl sulphoxide, dimethyl formamide, tetrahydrofuran;

Powders, such as chalk, talc, fullers earth, kaolin, starch, gums, colloidal silica sodium polyacrylate, tetra alkyl and/or trialkyl aryl ammonium smectites, chemically modified magnesium aluminum silicate, organically modified montmorillonite clay, hydrated aluminum silicate, fumed silica, carboxyvinyl polymer, sodium carboxymethyl cellulose, ethylene glycol monostearate, ethylene glycol distearate;

The cosmetically acceptable vehicle will usually form from 10 to 99.999%, preferably from 50 to 99% by weight of the emulsion, and can, in the absence of other cosmetic adjuncts, form the balance of the composition.

Hair Lightening Agent

The composition according to the invention can also optionally comprise a hair lightening agent.

It will be appreciated that following topical application of the composition to remove unwanted hair, regrowth of hair will generally occur unless the composition is reapplied repeatedly to prevent regrowth. When the hair is normally dark in colour, regrowth of hair at the site of treatment will generally be more noticeable than hair which is normally light in colour. It can accordingly be advantageous to incorporate in the composition of the invention a hair lightening or bleaching agent that will ensure that any hair that does regrow is itself light in colour and therefore less noticeable.

A particularly preferred hair lightening agent that can optionally be employed for this purpose is kojic acid. A suitable amount of kojic acid is from 0.1 to 20% by weight of the composition.

Conventional Hair Removal Ingredients

The composition according to the invention can also optionally comprise a conventional hair removal ingredient such as thioglycollate, in an amount sufficient to remove unwanted hair or in an amount of less than this. Thus, in spite of the resistance expressed by some consumers to the use of conventional hair removal products such as those containing thioglycollate at high pH and available for example under the trade names: "VEET" and "NAIR", there can be an advantage in combining the enzyme inhibitors of the present invention with thioglycollate as a traditional hair remover, in order to obtain the best results. Alternatively, a two step procedure can be employed in which a conventional thioglycollate hair remover is first applied to the skin to remove unwanted hair, and then a composition according to this invention, with or without further thioglycollate, is applied to the skin to eliminate hair regrowth.

Antiperspirants and Deodorants

The composition according to the invention can also optionally comprise one or more conventional antiperspirant or deodorant active substances, which can be of particular value if the composition is to be used on the underarm (axilla). Such compositions can thus be used regularly, for example on a daily basis on the underarm, not only to prevent unwanted hair growth, but also to reduce or eliminate perspiration and/or to reduce or eliminate body malodour.

Examples of conventional antiperspirant actives include astringent metallic salts, such as aluminum chloride, aluminum chlorohydrate, activated (or aged) aluminum chlorohydrate (also known as AACH) and zirconium salts as are regularly used in antiperspirant products. Alternatively, with the current trend away from using astringent metallic salts, more 'natural antiperspirents', such as water-absorbent materials, which function by absorbing perspiration as it emerges from the skin surface, rather than preventing its emergence by blocking the sebaceous ducts, are now gaining in popularity. Examples of water absorbent: antiperspirant materials include polymers that possesses the ability to absorb an amount of moisture at least equal to their own weight, such as chemically modified cellulose for example AKUCELL (Trade mark), cross-linked carboxymethylcellulose, for example AQUALON (Trade Mark) and carboxymethylated potato starch, for example FOXSORB (Trade Mark).

Examples of conventional deodorants include antimicrobial agents, such as cetyltrimethylammonium bromide, cetylpyridinium chloride, sodium N-lauroyl sarcosine, 3,4,4'-trichlorocarbanilide, and 2,4,4'-trichloro-2''-hydroxydiphenyl ether.

OTHER OPTIONAL SKIN BENEFIT MATERIALS AND COSMETIC ADJUNCTS

A particularly convenient form of the composition according to the invention is an emulsion, in which case an oil or oily material will normally be present, together with an emulsifier to provide either a water-in-oil emulsion or an oil-in-water emulsion, depending largely on the average hydrophilic-lyophilic balance (HLB) of the emulsifier employed.

Oil or Oily Material

The composition according to the invention can optionally comprise one or more oils or other materials having the properties of an oil.

Examples of suitable oils include mineral oil and vegetable oils, and oil materials, such as those already proposed herein as emollients. Other oils or oily materials include silicone oils, both volatile and nonvolatile, such as polydimethyl siloxanes.

The oil or oily material, when present for the purposes for forming an emulsion, will normally form up to 90%, preferably from 10 to 80% by volume of the composition.

Emulsifier

The composition according to the invention can also optionally comprise one or more emulsifiers the choice of which will normally determine whether a water-in-oil or and oil-in-water emulsion is formed.

When a water-in-oil emulsion is required, the chosen emulsifier or emulsifiers should normally have an average HLB value of from 1 to 6. When an oil-in-water emulsion is required, a chosen emulsifier or emulsifiers should have an average HLB value of >6.

Examples of suitable emulsifiers are set below in Table 2 in which the chemical name of the emulsifiers is given together with an example of a trade name as commercially available, and the average HLB value.

TABLE 1

| Chemical Name of Emulsifer | Trade Name | HLB Value |
|---|---|---|
| Sorbitan trioleate | Arlacel 85 | 1.8 |
| Sorbitan tristearate | Span 65 | 2.1 |
| Glycerol monooleate | Aldo MD | 2.7 |
| Glycerol monostearate | Atmul 84S | 2.8 |
| Glycerol monolaurate | Aldo MC | 3.3 |
| Sorbitan sesquioleate | Arlacel 83 | 3.7 |
| Sorbitan monooleate | Arlacel 80 | 4.3 |
| Sorbitan monostearate | Span 60 | 4.7 |
| Poloxyethylene (2) stearyl ether | Brij 72 | 4.9 |
| Poloxyethylene sorbitol beeswax derivative | G-1702 | 5 |
| PEG 200 dilaurate | Eraerest 2622 | 6.3 |
| Sorbitan monopalmitate | Arlacel 40 | 6.7 |
| Polyoxyethylene (3.5) nonyl phenol | Emulgen 903 | 7.8 |
| PEG 200 monostearate | Tegester PEG 200 MS | 8.5 |
| Sorbitan monolaurate | Arlacel 200 | 8.6 |
| PEG 400 dioleate | Tegester PEG 400-DO | 8.8 |
| Polyoxyethylene (5) monostearate | Ethofat 60-16 | 9.0 |
| Polyoxyethylene (4) sorbitan monostearate | Tween 61 | 9.6 |
| Polyoxyethylene (4) lauryl ether | Brij 30 | 9.7 |
| Polyoxyethylene (5) sorbitan monooleate | Tween 81 | 10.0 |
| PEG 300 monoolealte | Neutronyx 834 | 10.4 |
| Polyoxyethylene (20) sorbitan tristearate | Tween 65 | 10.5 |
| Polyoxyethylene (20) sorbitan trioleate | Tween 85 | 11.0 |
| Polyoxyethylene (8) monostearate | Myrj 45 | 11.1 |
| PEG 400 monooleate | Eraerest 2646 | 11.7 |
| PEG 400 monostearate | Tegester PEG 400 | 11.9 |
| Polyoxyethylene 10 monooleate | Ethofat 0/20 | 12.2 |
| Polyoxyethylene (10) stearyl ether | Brij 76 | 12.4 |
| Polyoxyethylene (10) cetyl ether | Brij 56 | 12.9 |
| Polyoxyethylene (9.3) octyl phenol | Triton X-100 | 13.0 |
| Polyoxyethylene (4) sorbitan monolaurate | Tween 21 | 13.3 |
| PEG 600 monooleate | Eraerest 2660 | 13.7 |
| PEG 1000 dilaurate | Kessco | 13.9 |
| Polyoxyethylene sorbitol lanolin derivative | G-1441 | 14.0 |
| Polyoxyethylene (12) lauryl ether | Ethosperse LA-12 | 14.4 |
| PEG 1500 dioleate | Pegosperse 1500 | 14.6 |
| Polyoxyethylene (14) laurate | Arosurf HFL-714 | 14.8 |
| Polyoxyethylene (20) sorbitan monostearate | Tween 60 | 14.9 |
| Polyoxyethylene 20 sorbitan monooleate | Tween 80 | 15.0 |
| Polyoxyethylene (20) stearate | Myrj 49 | 15.0 |
| Polyoxyethylene (20) stearyl ether | Brij 78 | 15.3 |
| Polyoxyethylene (20) sorbitan monopalmitate | Tween 40 | 15.6 |
| Polyoxyethylene (20) cetyl ether | Brij 58 | 15.7 |
| Polyoxyethylene (25) oxypropylene monostearate | G-2162 | 16.0 |
| Polyoxyethylene (20) sorbitol monolaurate | Tween 20 | 16.7 |
| Polyoxyethylene (23) lauryl ether | Brij 35 | 16.9 |
| Polyoxyethylene (50) monostearate | Myrj 53 | 17.9 |
| PEG 4000 monostearate | Pegosperse 4000 MS | 18.7 |

The foregoing list of emulsifiers is not intended to be limiting and merely exemplifies selected emulsifiers which are suitable for use in accordance with the invention.

It is to be understood that two or more emulsifiers can be employed if desired.

The amount of emulsifier or mixtures thereof, to be incorporated in the composition of the invention, when appropriate is from 1 to 50%, preferably from 2 to 20% and most preferably from 2 to 10% by weight of the composition.

Water

The composition of the invention can also comprise water, usually up to 90%, preferably from 5 to 80% by volume. Water can function as the cosmetically acceptable vehicle.

Silicone Surfactant

The composition of the invention can also optionally comprise a high molecular weight silicone surfactant which can also act as an emulsifier, in place of or in addition to the optional emulsifier(s) already mentioned.

The silicone surfactant is a high molecular weight polymer of dimethyl polysiloxane with polyoxyethylene and/or polyoxypropylene side chains having a molecular weight of from 10,000 to 50,000 and having the structure:

$$CH_3-Si(CH_3)_2-O-[Si(CH_3)(R)-O]_x-[Si(CH_3)(R')-O]_y-Si(CH_3)_2-CH_3$$

where R is a $C_{1-18}$ alkyl group and
R' is a polyether group having the structure:
—$CH_3H_5O(C_2H_4O)_a(CH_3C_2H_3O)_bR''$
where R" is H or a $C_{1-18}$ alkyl group,
a has a value of from 9 to 115,
b has a value of from 0 to 50,
x has a value of from 133 to 673,
y has a value of from 25 to 0.25.

Preferably, the dimethyl polysiloxane polymer is one in which:
a has a value of from 10 to 114
b has a value of from 0 to 49
x has a value of from 388 to 402
y has a value of from 15 to 0.75
one of groups R' and R" being lauryl, and the other having a molcular weight of from 1000 to 5000.

A particularly preferred dimethyl polysiloxane polymer is one in which:
a has the value 14
b has the value 13
x has the value 249
y has the value 1.25

The dimethyl polysiloxane polymer is conveniently provided as a dispersion in a volatile siloxane, the dispersion comprising, for example, from 1 to 20% by volume of the polymer and from 80 to 99% by volume of the volatile siloxane. Ideally, the dispersion consists of a 10% by volume of the polymer dispersed in the volatile siloxane.

Examples of the volatile siloxanes in which the polysiloxane polymer can be dispersed include polydimethyl siloxane (pentamer and/or hexamer).

A particularly preferred silicone surfactant is cyclomethicone and dimethicone copolyol, such as DC 3225C Formulation Aid available from DOW CORNING. Another is laurylmethicone copolyol, such as DC Q2-5200, also available from Dow Corning.

The amount of silicone surfactant, when present in the composition will normally be up to 25%, preferably from 0.5 to 15% by weight of the emulsion.

Surfactant

The composition according to the invention can also optionally comprise a surfactant chosen from anionic, nonionic or amphoteric surfactant or mixtures thereof.

Suitable anionic surfactants for this purpose are the alkyl sulphates, alkyl ether sulphates, alkaryl sulphonates, alkyl succinates, alkyl sulphosuccinates, N-alkoyl sarcosinates, and alpha-olefin sulphonates, expecially their sodium, magnesium, ammonium and mono-, di- and triethanolamine salts. The alkyl groups generally contain from 8 to 18 carbon atoms and may be unsaturated. The alkyl ether sulphates may contain from one to 10 ethylene oxide or propylene oxide units per molecule, and preferably contain 2 to 3 ethylene oxide units per molecule.

Examples of suitable anionic surfactants include sodium lauryl sulphate, sodium oleyl succinate, ammonium lauryl sulphosuccinate, ammonium lauryl sulphate, sodium dodecylbenzene sulphonate, triethanolamine dodecylbenzene sulphonate and sodium N-lauryl sarcosinate. The most preferred anionic surfactants are sodium lauryl sulphate, sodium lauryl ether sulphate 2EO and 3EO, ammonium lauryl sulphate and ammonium lauryl ether sulphate 1EO, 2EO and 3EO.

The nonionic surfactants suitable for optional use in the composition of the invention may include condensation products of aliphatic ($C_8$–$C_{18}$) primary or secondary linear or branched chain alcohols or phenols with alkylene oxides, usually ethylene oxide and generally 6–30 EO.

Other suitable nonionics include mono or di alkyl alkanolamides or alkyl polyglucosides. Examples include coco mono or diethanoiamide, coco mono isopropanolamide, and coco di glucoside.

The amphoteric surfactants suitable for optional use in the composition of the invention may include alkyl amine oxides, alkyl betaines, alkyl amidopropyl betaines, alkyl mono- or dialkanolamides, alkyl sulphobetaines, alkyl glycinates and alkyl carboxyglycinates, wherein the alkyl groups have from 8 to 18 carbon atoms. Examples include lauryl amine oxide, cocomonoethanolamide, cocodiethanolamide, cocoimidopropyl betaine, cocodimethyl sulphopropyl betaine and preferably cocobetaine.

The surfactants when present in the composition of the invention form from 2 to 40% by weight, and preferably from 5 to 30% by weight.

Other Cosmetic Adjuncts

Examples of conventional adjuncts which can optionally be employed include antioxidants, such butyl hydroxy toluene; sunscreens, such as octyl methoxycinnamate and butylmethoxy di-benzoyl methane; humectants, such as glycerol, sorbitol, 2-pyrrolidone-5-carboxylate, dibutylphthalate, gelatin, polyethylene glycol, such as PEG 200–600; buffers, such as lactic acid together with a base such as triethanolamine or sodium hydroxide; waxes, such as beeswax, ozokerite wax, paraffin wax: plant extracts, such as Aloe vera, cornflower, witch hazel, elderflower, cucumber; thickeners; activity enhancers; colourants; and perfumes. Cosmetic adjuncts can form the balance of the composition.

Preservation of the Composition

The composition according to the invention is preferably preserved in such a manner that it will enjoy an extended shelf life following manufacture and prior to sale and use. Ideally the composition will have an indefinite shelf life.

It is accordingly apparent that the enzyme inhibitor is likely to be prone to attack by bacteria, moulds and fungi and other microbial influences, particularly at pH values near that of the skin that characterize the preferred composition. The shelf-life of the composition can therefore be unacceptably short due to the biodegradation of the inhibitor unless steps are taken to preserve the composition.

In order to be preserved, the composition should preferably be free, or substantially free, from viable microbial contaminants that are capable of resulting in microbial spoilage of the composition, and/or biodegradation of the inhibitor prior to topical application of the composition to mammalian skin or hair. It is to be understood, however, that the invention is also concerned with compositions, as herein defined, which may contain viable but dominant microorganisms, such as bacterial spores, provided that the conditions of preservation do not result in substantial proliferation of the microorganisms prior to use of the composition.

Examples of the methods that can be employed to achieve preservation of the composition, includes the following:

(i) Sterilization

The composition according to the invention can be preserved by sterilization to remove or kill substantially all viable microbial contaminants. This can be achieved for example by irradiation using a lethal dose of gamma rays, by heat sterilization or by ultrafiltration using techniques that are well established in the pharmaceutical industry.

(ii) Chemical Preservative

The composition according to the invention can also be preserved by including in it a chemical preservative which functions to prevent the growth of or kill bacteria, fungi or other microorganisms.

Examples of chemical preservatives include ethanol, benzoic acid, sodium benzoate, sorbic acid, potassium sorbate, sodium propionate and the methyl, ethyl, propyl and butyl esters of p-hydroxybenzoic acid. The amount of chemical preservative that can be incorporated in the composition according to the invention will generally be from 0.05 to 5%, preferably from 0.1 to 2% by weight, the amount chosen being sufficient to arrest microbial proliferation.

(iii) Water Activity Depressants

The composition according to the invention can also be preserved by the inclusion of a water activity depressant such as glycerol, propylene glycol, sorbitol, sugars and salts, for examples alkali metal halides sulphates and carboxylates. When employing a water activity depressant, sufficient should be incorporated in the composition according to the invention to reduce the water activity ($\alpha$) from 1 to <0.9, preferably to <0.85 and most preferably <0.8, the lowest of these values being that at which yeasts, moulds and fungi will not proliferate.

Use of the Inhibitor of Glutamine Metabolism for Reducing or Retarding Hair Growth or for Eliminating Hair from the Skin.

The invention accordingly also provides for the use of an inhibitor of glutamine metabolism, as herein defined, for topical application to mammalian skin or hair for reducing or retarding hair growth, or for eliminating unwanted hair from the skin surface.

The composition according to the invention is primarily intended for topical application to the skin of the human subject, particularly the legs, axillae and face, in order to eliminate unwanted hair, or at least to reduce or retard hair growth. The compositions can also be applied profilactically to the skin to prevent subsequent hair regrowth.

The amount of the composition and the frequency of application to the skin can vary widely depending on personal needs, but it is suggested as an example that topical application of from 0.1 to 5 g daily containing from 0.00001 to 1 g of a selected inhibitor of glutamine metabolism, will in most cases result in desired loss of unwanted hair and maintenance of the skin in a hairless condition.

PRODUCT FORM AND PACKAGING

The topical skin and/or hair treatment composition of the invention can be formulated as a liquid or gel, or as a lotion having a viscosity of from 4,000 to 10,000 mPas, a fluid cream having a viscosity of from 10,000 to 20,000 mPas or a cream having a viscosity of from 20,000 to 100,000 mPas, or above.

Although the composition of the invention is primarily intended to be formulated as a product for the removal of unwanted hair from the skin, it can with the inclusion of suitable adjuncts be formulated to function, for example, as an antiperspirant, deodorant, sun care product, or a shaving product, such as a shaving mousse.

The composition can be packaged in a container to suit its viscosity and intended use by the consumer. For example, a liquid, gel, lotion or fluid cream can be packaged in a bottle or a roll-ball applicator or a propellant-driven aerosol device or a container fitted with a pump suitable for finger operation. This composition can be packaged in a bottle or sachet. When the composition is a cream, it can simply be stored in a non-deformable bottle or squeeze container, such as a tube or a lidded jar.

The invention accordingly also provides a closed container containing a cosmetically acceptable composition as herein defined.

Process

The invention also provides a process for preparing a depilatory composition which comprises the steps of mixing an effective amount of an inhibitor of glutamine metabolism, as herein defined, together with a cosmetically acceptable carrier for the inhibitor.

Evidence to Demonstrate the Inhibition of Glutamine Metabolism in Hair, In Vitro As has been stated earlier, the conversion of succinate to fumarate is catalyzed by the enzyme succinate dehydrogenase, whose activities can be inhibited by the presence of an effective amount of malonic acid. This acid is accordingly an important enzyme inhibitor which interferes with the conversion of glutamine to pyruvate, since this pathway involves the formation of both fumarate and malate before pyruvate is reached.

The effect of malonic acid in this role has therefore been verified by an in vitro technique involving a study of the growth of isolated, viable hair follicles.

The technique employed was as follows:

Human scalp hair follicles were isolated as described by Philpott et al., in J Cell Sci 97, 463–471 (1990). Ten follicles from each of two patients and five from a third patient were incubated in the presence and absence of 2.5 mM malonic acid [0.026% w/v], in growth medium (Williams E medium containing L-Glutamine (2 mM) and antibiotics, all available from Flow Laboratories, supplemented with insulin (10 $\mu$g/ml) and hydrocortisone (10 ng/ml). The lengths of the hair follicles were recorded on day 0, 1, 2, 5, 6, 7, 8, 9 using an eyepiece graticule and inverted microscope and the mean cumulative growth calculated for each treatment group. Results are shown in FIG. 1 with error bars representing the standard error of the means (3.E.M).

Figure 1:
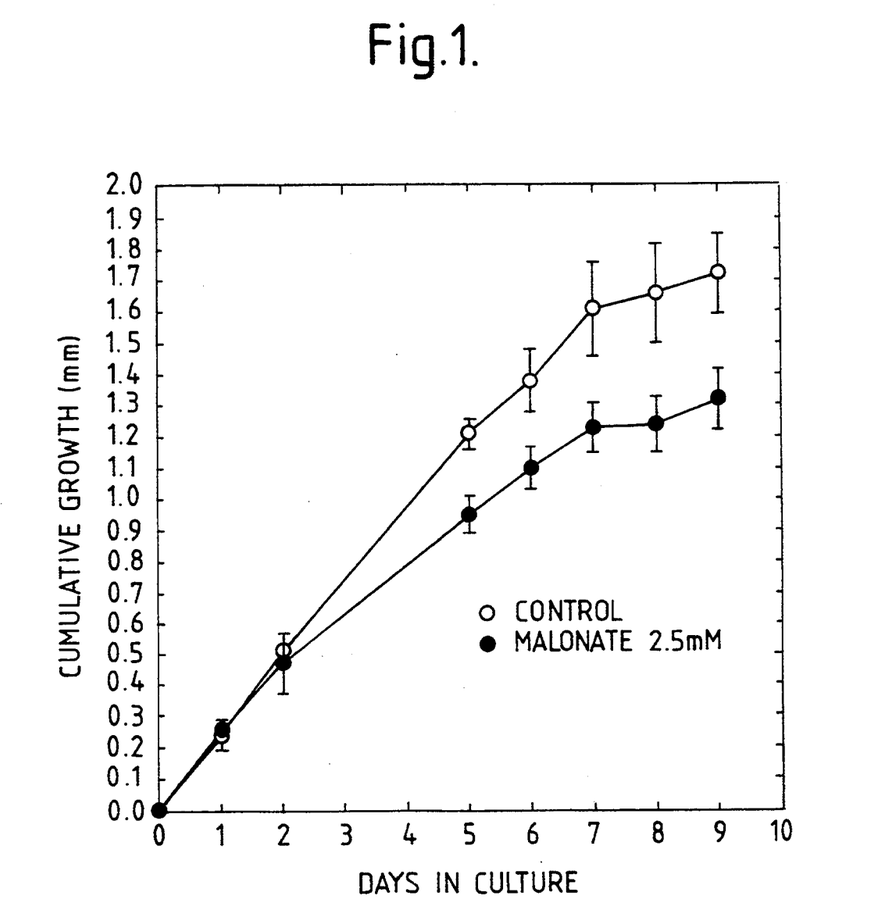
In FIG. 1, the mean cumulative hair growth (mm) for all the hair follicles is shown on the ordinate and the duration of the experiment (9 days culture in supplemented Williams E medium) is shown on the abscissa.

As can be seen by inspection of FIG. 1, the rate of hair growth in vitro is significantly reduced over the test period in the presence of 2.5 mM malonic acid, as compared with the control.

In addition, two other inhibitors were tested using the same technique as described above. These inhibitors were meso-tartaric acid, which inhibits the enzyme fumarase and inhibits conversion of fumarate to malate, and hydroxy malonic acid (tartronic acid), which inhibits malic enzyme and inhibits conversion of oxaloacetate to pyruvate. Results show that these inhibitors are not as potent as malonic acid, however, they appear to behave synergistically. Potency may relate to the position in the pathway of glutamine metabolism at which they exert their effect.

The hair growth inhibiting effect of all three inhibitors tested after 7 days culture in supplemented Williams E medium is shown in Table 2 below.

TABLE 2

| Inhibitor | Average amount of hair grown in one week (mm) | Hair grown in one week in-vitro as a percentage of control (average) | Number of hair follicles examined |
|---|---|---|---|
| Malonic Acid 2.5 mM (0.026% w/v) | 1.61 mm control 1.23 mm test | 76.4% | 25 |
| Meso Tartaric Acid 3.5 mM (0.0375% w/v) | 2.01 mm control 1.95 mm test | 97.3% | 22 |
| Meso Tartaric Acid 10 mM (0.15% w/v) | 2.00 mm control 1.48 mm test | 75.1% | 22 |

TABLE 2-continued

| Inhibitor | Average amount of hair grown in one week (mm) | Hair grown in one week in-vitro as a percentage of control (average) | Number of hair follicles examined |
|---|---|---|---|
| Hydroxymalonic Acid 2.5 mM (0.03% w/v) | 2.01 mm control 1.98 mm test | 97.9% | 22 |
| Hydroxymalonic Acid 10 mM (0.12% w/v) | 2.16 mm control 2.08 mm test | 96.3% | 10 |
| Hydroxymalonic Adic 2.5 mM plus Meso Tartaric Acid 2.5 mm | 2.16 mm control 1.89 mm test | 87.5% | 10 |

EXAMPLES

The invention is illustrated by the following examples, each of which provides a composition comprising one or more specific enzyme inhibitors of glutamine metabolism in accordance with the invention.

Example 1

This Example illustrates a lotion according to the invention which is suitable for topical application to the skin in order no eliminate hair growth.

The lotion has the following formulation:

|  | % w/v |
|---|---|
| 6-diazo-5-oxonorleucine | 8 |
| Water | to 100 |
| Perfume | q.s. |

Example 2

This Example illustrates a hair retarding tonic which is suitable for application to skin of the legs or axillae.

The hair retarding tonic has the following formulation:

|  | % w/v |
|---|---|
| 3-carboxy-5-bromofurorate | 2 |
| Ethanol | 60 |
| Water | to 100 |
| Perfume | q.s. |

Example 3

This Example also illustrates a lotion which is suitable for topical application to the underarm.

The lotion has the following formulation:

|  | % w/v |
|---|---|
| Copper (II) acetate | 1 |
| Propan-2-ol | 10 |
| Water | to 100 |
| Perfume | q.s. |

Example 4

This Example also illustrates a hair remover which is suitable for application to the skin.

The hair remover has the following formulation:

|  | % w/v |
|---|---|
| Vanadium sulphate | 1 |
| Ethanol | 20 |
| Water | to 100 |
| Perfume | q.s. |

Examples 5 to 7

The following formulations represent lotions which can be used topically in the removal of hair from the face, legs or axillae.

|  | % w/v | | |
|---|---|---|---|
|  | 5 | 6 | 7 |
| Hydroxyethyl cellulose | 0.4 | — | 0.4 |
| Absolute ethanol | 25 | 25 | 25 |
| Propane-1,2-diol | — | — | 38.4 |
| Butane-1,3-diol | 38.4 | 38.8 | — |
| Paramethyl benzoate | 0.2 | 0.2 | 0.2 |
| Malonic acid | 7.5 | — | — |
| Meso-tartaric acid | — | 7.0 | — |
| Fluoromalic acid | — | — | 6.5 |
| N-acetyl proline | 0.6 | 0.6 | 0.6 |
| Perfume | 1 | 1 | 1 |
| Water | to 100 | 100 | 100 |

Example 8

This Example illustrates a water-in-oil emulsion containing an enzyme inhibitor according to the invention, which is useful for removing hair from the body surface.

The emulsion consisted of 10% by volume oily phase and 90% by volume aqueous phase.

The oily phase and the aqueous phase had the following constitution:

|  | % w/v |
|---|---|
| Oily phase | |
| Sorbitan monooleate | 20 |
| Quaternium-18 hectorite | 5 |
| Liquid paraffin | 75 |
| Aqueous phase | |
| malonic acid | 5.0 |
| Xanthan gum | 1 |
| Preservative | 0.3 |
| Perfume | q.s. |
| Sodium chloride (1% w/w solution) | to 100 |

The emulsion was prepared by taking 10 parts by volume of the oily phase and to it adding slowly with stirring 90 parts by volume of the aqueous phase.

Example 9

This Example also illustrates a lotion which is suitable for topical application to the skin.

The lotion has the following formulation:

|  | % w/v |
|---|---|
| Hydroxymalonic acid | 5.0 |
| Propan-2-ol | 10 |
| Ethanol | to 100 |

Example 10

This example illustrates a water-in-oil emulsion containing two enzyme inhibitors according to the invention, which is useful for removing hair from the body surface.

The emulsion consisted of 10% by volume oily phase and 90% by volume aqueous phase.

The oily phase and the aqueous phase had the following constitution:

|  | % w/v |
|---|---|
| Oily phase | |
| Sorbitan monooleate | 20 |
| Quaternium-18 hectorite | 5 |
| Liquid paraffin | 75 |
| Aqueous phase | |
| malonic acid | 2.5 |
| Hydroxymalonic acid | 2.5 |
| Xanthan gum | 1 |
| Preservative | 0.3 |
| Perfume | q.s. |
| Sodium chloride (1% w/w solution) | to 100 |

The emulsion was prepared by taking 10 parts by volume of the oily phase and to it adding slowly with stirring 90 parts by volume of the aqueous phase.

Example 11

This example illustrates a shaving mousse product according to the invention. The product contained the following ingredient.

| Ingredient | % w/v |
|---|---|
| Triethanolamine stearate | 8 |
| Sodium stearate | 1 |
| Potassium stearate | 4.6 |
| Malonic acid | 7.0 |
| Water | 20 |
| Perfume | q.s. |
| Propellant | to 100 |

Example 12

This example illustrates a roll-on antiperspirant in accordance with the invention. The roll-on lotion contained the following ingredients.

| | Ingredient | % w/v |
|---|---|---|
| A. | Magnesium aluminium silicate | 1 |
| | Water | 44 |
| | Malonic acid | 5 |
| B. | Glyceryl monostearate | 8 |
| C. | Aluminium chlorohydrate (50% aq. soln) | 40 |
| D. | Volatile silicone | 2 |

Procedure

Add magnesium aluminum silicate and malonic acid to water slowly, agitating continually until smooth, and heat to 70° C. Heat B, to 75° C. and add to A. Mix until temperature has fallen to 50° C. Heat C. to 50° C. and add to A.+B. Mix until product has reached room temperature (20° C.). Add D. and stir for 15 minutes.

The lotion prepared as above is then dispensed into a roll-ball applicator to provide the finished roll-on product.

The same lotion is also suitable for impregnating a fabric or tissue for use as a wipe.

We claim:

1. A composition suitable for topical application to mammalian skin for reducing, retarding or eliminating hair growth, which comprises:
   i) an effective amount of an inhibitor of glutamine metabolism which inhibitor is an agent for inhibiting at least one enzyme involved in the conversion of glutamine to lactate in mammalian skin or hair the enzyme selected from the group consisting of
   glutaminase which converts glutamine to glutamate;
   glutamate dehydrogenase which converts glutamate to α-ketoglutarate;
   α-ketoglutarate decarboxylase which converts α-ketoglutarate to succinyl CoA;
   succinyl CoA synthetase which converts succinyl CoA to succinate;
   succinate dehydrogenase which .Converts succinate to fumarate;
   fumarase which converts fumarate to malate;
   malate dehydrogenase which converts malate to oxaloacetate;
   malic enzyme which converts oxaloacetate to pyruvate; and mixtures thereof, and
   ii) a cosmetically acceptable vehicle for the inhibitor.

2. A composition according to claim 1, in which the glutaminase inhibitor is 6-diazo-5-oxonorleucine.

3. A composition according to claim 1, in which the glutamate dehydrogenase inhibitor is 3-carboxy-5-bromofuroic acid.

4. A composition according to claim 1, in which the α-ketoglutarate decarboxylase inhibitor is copper (II) acetate.

5. A composition according to claim 1, in which the succinyl CoA synthetase inhibitor is vanadium sulphate.

6. A composition according to claim 1, in which the succinate dehydrogenase inhibitor is malonic acid.

7. A composition according to claim 1, in which the fumarase inhibitor is meso-tartaric acid.

8. A composition according to claim 1, in which the malate dehydrogenase inhibitor is fluoromalic acid.

9. A composition according to claim 1, in which the malic enzyme inhibitor is hydroxymalonic acid.

10. A composition according to claim 1, in which the malate enzyme inhibitor is hydroxymalonic acid.

11. A composition according to claim 1, which further comprises a hair lightener.

12. A composition according to claim 11, in which the hair lightener is kojic acid.

13. A composition according to claim 1, which further comprises a thioglycollate.

14. A composition according to claim 1, which comprises not more than 5.0 weight part of inhibitor per 100 volume parts of the composition.

15. A composition according to claim 14 which comprises not more than 1.0 weight parts of inhibitor per 100 volume parts of the composition.

16. A method of reducing, retarding, or eliminating hair growth on mammalian skin, the method comprising applying topically to the skin an inhibitor of glutamine metabolism in mammalian skin or hair, which inhibitor is an agent for inhibiting at least one enzyme involved in the conversion of glutamine to lactate in mammalian skin or hair the enzyme selected from the group consisting of
   glutaminase which converts glutamine to glutamate;

glutamate dehydrogenase which converts glutamate to α-ketoglutarate;

α-ketoglutarate decarboxylase which converts α-ketoglutarate to succinyl CoA;

succinyl CoA synthetase which converts succinyl CoA to succinate;

succinate dehydrogenase which converts succinate to fumarate;

fumarase which converts fumarate to malate;

malate dehydrogenase which converts malate to oxaloacetate:

malic enzyme which converts oxaloacetate to pyruvate; and mixtures thereof.

* * * * *